United States Patent [19]

D'Hinterland et al.

[11] Patent Number: 5,830,994
[45] Date of Patent: Nov. 3, 1998

[54] PEPTIDE DERIVATIVES OF ALPHA-MSH AND THEIR APPLICATION

[75] Inventors: Lucien Dussourd D'Hinterland; Anne-Marie Pinel, both of Toulouse, France

[73] Assignee: Institut Europeen De Biologie Cellulaire, Ramonville-Saint-Agne, France

[21] Appl. No.: 446,817

[22] PCT Filed: Sep. 22, 1994

[86] PCT No.: PCT/FR94/01108

§ 371 Date: May 22, 1995

§ 102(e) Date: May 22, 1995

[87] PCT Pub. No.: WO95/08564

PCT Pub. Date: May 30, 1995

[30] Foreign Application Priority Data

Sep. 22, 1993 [FR] France .................................. 93 11281

[51] Int. Cl.⁶ .......................... A01N 61/00; A01N 37/18; A61K 38/00; C07K 1/00
[52] U.S. Cl. .............................. 530/200; 530/350; 514/1; 514/2
[58] Field of Search ..................... 530/300, 350; 514/1, 2

[56] References Cited

U.S. PATENT DOCUMENTS 4,647,655  3/1987  Axen et al. ............................. 530/390
5,017,368  5/1991  Sugiyama et al. ........................ 424/70

FOREIGN PATENT DOCUMENTS 0 292 291  11/1988  European Pat. Off. .

OTHER PUBLICATIONS

Hasunuma, *Chemical Abstracts*, vol. 108: 26828Z p. 321 (1988).

Tuaillon et al., *Journal of Immunology*, vol. 148:445–450 (1992).

International Search Report dated Jan. 25, 1995 for parent PCT application WO95/08564.

French Search Report dated Jun. 17, 1994 for priority application FR 93 11281.

*Primary Examiner*—Ardin H. Marschel
*Assistant Examiner*—Jezia Riley
*Attorney, Agent, or Firm*—Dechert Price & Rhoads

[57] ABSTRACT

Provided is a compound containing a peptide of at least 4 amino acids including the following sequence: His Phe* Arg, wherein Phe* represents phenylalanine or a halogenated derivative of phenylalanine the said peptide being conjugated with thioctic acid, dihydrolioic acid, or N-lipoyl-lysine, in the form of the corresponding salts, esters or amides. In particular, compounds with anti-allergic and anti-inflammatory activities on the one had, and melanogenesis-activating activities on the other, are described.

22 Claims, No Drawings

PEPTIDE DERIVATIVES OF ALPHA-MSH AND THEIR APPLICATION

The present invention has especially peptide derivatives of α-MSH ("Melanocyte Stimulating Hormone"), presented in Lipoyl-Peptide form.

α-MSH and its homologs have been the subject of numerous publications or even of therapeutic trials without this resulting in the production of a medicinal product.

The principal reason is the extreme ubiquitousness of α-MSH depending on the administered doses and the routes of administration.

Furthermore, the absence of a dose-effect relationship (which is the case for numerous peptide hormones) seriously complicates its therapeutic use.

The cell receptors for α-MSH and its homologs are of the G type and intracellular transduction occurs according to the cyclic AMP cycle. The activation of these cell receptors is essentially inversely proportional to the peptide hormone doses accepted by the structures of the membrane receptor.

The present invention is based on the search for peptide structures specifically orientated towards anti-allergic and anti-inflammatory activities on the one hand, and melanogenesis-activating activities on the other, excluding any other pharmacological effect, especially at the level of the central nervous system, as well as the peripheral nervous system.

More particularly, the present invention relates to a compound containing a peptide sequence comprising at least one sequence of 4 amino acids obtained from α-MSH, the amino acids being in natural or nonnatural form, the said sequence being conjugated with thioctic acid or a derivative of this acid, in the form of the corresponding salts, esters or amides.

The sequence of α-MSH is the following:
N-acetyl-Ser-Tyr-Ser- Met-Glu- His-Phe-Arg-Trp-Gly-Lys-Pro-Val-NH$_2$ -

In this definition, as in the text that will follow, the amino acids may be in D, L or D,L form and the nonnatural forms of the amino acids correspond to derivatives, especially substituted derivatives.

Thioctic acid or α-lipoic acid may be in oxidized form:

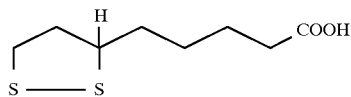

or in the form of a dihydrolipoic derivative:

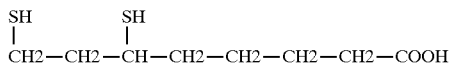

Among the derivatives of this acid, the N-lysine derivative of the oxidized or dihydro form must be mentioned.

One of the principal objects of the present invention is the therapeutic application via the topical (cutaneous) route of the preceding derivatives.

These compounds are molecules capable of crossing the cutaneous barrier and of presenting the peptide fraction to the cell receptors, inducing a biological response of the dose/effect relationship type.

These low molecular weight peptides whose amino acid sequences have been modified, are linked in the form of salts, esters or amides to active biochemical groups, playing a vital role in the tricarboxylic cycle (at the level of the mitochondria in particular). These cofactors are lipoic or thioctic acids in oxidized or reduced form and their Lipoyl-Lysine derivatives, which are naturally linked by covalent bonding to the polypeptide chains of the cellular enzymatic system.

More specifically, the present invention relates to peptides of 4 to 6 amino acids linked in the form of Lipoyl-Peptides and of Lipoyl-Lysyl-Peptides with anti-allergic, anti-inflammatory and melanogenesis-activating activity.

The compounds according to the invention preferably have the peptide sequence containing at least the following sequence:

Y is [-] selected from the group consisting of:

Trp - Gly - OH,

Trp - Gly - NH2,

Trp—NH2, and

Tr—OH, in which Phe represents phenylalanine or a halogenated derivative of phenylalanine, it being possible for the amino acids to be in D, L or D,L form, and in particular they may be compounds having the formula:

[Lip] X - His - Phe - Arg - Y in which
Lip is thioctic acid or one of its derivatives,
X is Glu, OH or NH2,
Y is Trp - Gly - OH Trp - Gly - NH2

Trp - NH2

Trp - OH

Phe is homoPhe or p-fluoroPhe, the amino acids being in D, L or D,L form.

The invention relates more particularly to the following compounds:

| | |
|---|---|
| [(DL) Lip] Glu - His - D.homoPhe - Arg - Trp - Gly - NH2 | I |
| [(DH Lip] Glu - His - D.homoPhe - Arg - Trp - Gly - NH2 | II |
| [(DL) Lip] Glu - His - paraFluoroPhe - Arg - Trp - Gly - NH2 | III |
| [(DL) Lip] His - D.homoPhe - Arg - Trp - NH2 | IV |
| [N.Lipoyl-Lysine] Glu - His - D.homoPhe - Arg - Trp - Gly - NH2 | V |
| [N.lipoyl-Lysine] His - D.homoPhe - Arg - Trp - Gly - NH2 | VI |
| [N.lipoyl-Lysine] His - D.homoPhe - Arg - Trp - NH2 | VII | as well as the derivatives of these molecules in the form of salts of esters or of amides.

In the formulae, the position of thioctic acid corresponds to the ester or amide derivative, the acid fraction of thioctic acid assuring the bonding.

The amino acid sequences mentioned above may be natural amino acid sequences or nonnatural amino acid sequences. Likewise, in some cases it is possible that some of these amino acids contain functional groups; for example they are glycosylated and/or sulfated.

It should be understood that all of these forms are covered by the present description.

The present invention also relates to pharmaceutical or dermocosmetic compositions containing a compound as defined above.

The pharmaceutical compositions may be in a form which can be administered orally or parenterally, intraperitoneally or as an injection in particular, but preferably in a form which can be administered via an external topical route.

These compositions may be in particular in the form of a cream, a spray or a lotion for example and may contain known excipients and optionally other active ingredients.

The compounds according to the present invention are useful especially in the prevention and treatment of allergies and inflammations.

The Peptide III, whose sequence has in the 3-position the amino acid paraFluoroPhenyl, is particularly oriented towards an anti-allergic and anti-inflammatory activity, by immunosuppression of Monokines (IL1, IL6, TNF-α).

The dermocosmetic compositions are preferably in the form of a solution, a lotion, an emulsion or a cream which can be used in particular as accelerator for tanning the skin without exposure to ultraviolet rays.

The Peptides II and IV whose sequences possess in the 3- and 2-positions of the amino acid D.homoPhenyl are particularly orientated towards a stimulation of the processes of melanogenesis and of Tyrosinase activation.

The Peptide sequences according to the present invention can be obtained by any of the processes known to a person skilled in the art, especially by processes of chemical synthesis in which thioctic acid can be integrated. In any case, given the small size of the Peptides, the chemical synthesis is completely possible and makes it possible to obtain very pure products.

EXAMPLE 1
Synthesis of compound 1

1 - [(DL) Lip] Glu - His - D.homoPhe - Arg - Trp - Gly - NH2

The synthesis is carried out by the solid phase Merrifield method using an MBHA resin and as protecting group FMOC (fluorenylmethoxycarbonyl).

The amino acid derivatives used are:

FMOC - Gly - OH,

FMOC - Arg (Tos) - OH,

FMOC - Trp - OH,

FMOC - D.homo.Phe - OH,

FMOC - His - (Trt) - OH

FMOC - Glu - chex) - OH which are coupled using BOP as coupling agent.

Each amino acid is used in excess (x2) as well as BOP (x2) and each coupling is repeated twice.

The Lipoic acid is coupled in a similar manner, the FMOC group is removed at each stage with piperidine (20% in dimethylformamide).

The final deprotection is carried out in two stages:
a) Trifluoroacetic acid (twice×5 minutes)
b) anhydrous hydrofluoric acid/p-Cresol 95.5 (45 minutes)

The crude compound obtained with a 78% yield is taken up in a water/95.5% acetic acid mixture and is then freeze-dried.

The compound 1 obtained has a purity of 82% (HPLC). 100 mg of this compound are purified by HPLC using a C18 column 65 mg of pure product are obtained.

Retention time=17.04 minutes under the following conditions:

—C8 column (250 mm×5 mm)), UV detection 210 nm
—solvent phosphate buffer Triethylamine-acetonitrile 10–60% over 15 minutes—flowrate 1.4 ml/minute.

Analysis of the amino acids:

Glu 1.02 - Gly 1.01 - His 1.00 - Arg 0.94 - D.homo.Phe 1.03 -

Tryptophan was not determined because it is degraded during the acid hydrolysis.

Mass spectrum (FAB+) 1018.4/1126.5

EXAMPLES 2 AND 3

By replacing DL-lipoic acid with DH-lipoic acid, compound 2 is obtained:

[DH Lip] Glu - His - D.homoPhe - Arg - Trp - Gly - NH$_2$.

By replacing FMOC D.homoPhe - OH with FMOC ParafluoroPhe-OH, compound 3 is obtained:
[(DL) Lip] Glu - His - ParaFluoroPhe - Arg - Trp - Gly - NH2

EXAMPLE 4
Synthesis of compound 4

The procedure is carried out as in Example 1 in order to prepare:

[(DL) Lip] His - D.homoPhe - Arg - Trp - NH2

Physical constants . . .
m.p.—130° C. retention time 19.72 minutes
"Nucleosil" C18 column—UV—279 nm
Solvent TFA—0.1% Acetonitrile 75/20
flow rate—1.2 ml/minute
Analysis of the amino acids
His=0.80—Dh- Phe 1.11 Arg=0.96
Trp=not assayed—chemical mass—887.18

EXAMPLES 5 TO 7

By carrying out the procedure as above, the following are obtained:

compound 5 [N.Lipoyl-Lysine] Glu - His - D.homoPhe - Arg - Trp - Gly - NH2 compound 6 [N.Lipoyl-Lysine] His - D.homoPhe - Arg - Trp - Gly - NH2 compound 7 [N.Lipoyl-Lysine] His - D.homoPhe - Arg - Trp - NH2

EXAMPLE 8
Study of the immunosuppressive activity of the derivative compound 4 on the inhibition of the synthesis of Interleukin 1 "IL1" in mice.

The secretion of IL1 is induced by the parenteral administration of lipopolysaccharides "LPS" to BALB/C mice.

The release of bacterial lipopolysaccharides during microbial infections strongly induces the synthesis and the release in the body of the monokines Interleukins "1 IL1", Interleukin 6 "IL6" and of "Tumor-Necrosis-factor" TNF-α which are responsible for violent inflammatory reactions including septic shock.

Materials

Compound 4 (P-IV) is dissolved in physiological saline. It is assayed quantitatively by spectrophotometry at 280 nm (assay of Tryptophan) which allows an accurate assay of "P-IV" in the solutions which are stored at −25° C.

Lipopolysaccharides "LPS":

Extracts of Escherichia Coli serotype 0127 - B8 -"Ref. SIGMA - L3137" are used at the concentration of 6 mg/ml in physiological saline.

Animals:

BALB/C mice—females—5 weeks old, obtained from IFFA - CREDO subjected to a photoperiod of 12 hours of light per 24 hours water and feed ad libitum Methods:

Two techniques were developed in order to carry out this assay:

one based on a 5-day treatment used to demonstrate the anti-inflammatory activity of PIV (called "SHEEHAN" technique)

the other based on a single treatment, consequently much more rapid, will serve for the control of the PIV activity ("DAYNES" technique).

1—SHEEHAN technique a) dosage

Three dosages are studied:

1 ng of PIV in 0.2 ml of physiological saline (that is to say 5 ng/ml)

0.5 ng of PIV in 0.2 ml of physiological saline (that is to say 2.5 ng/ml)

0.1 ng of PIV in 0.2 ml of physiological saline (that is to say 0.5 ng/ml)

b) Treatment of the animals

It was carried out on mice separated into five batches of 5 animals:

one negative control batch
one positive control batch
three PIV batches (one per dosage)

The animals in the control batches receive an injection of 0.2 ml of physiological saline subcutaneously, the animals in the PIV batches receive an injection of the product at various dosages subcutaneously. This treatment takes place for 5 days.

c) Induction of IL1α

Forty-eight hours after the treatment with PIV, a sublethal dose of LPS (1.2 mg in 0.2 ml of physiological saline) is injected intraperitoneally into each animal in the PIV batches and in the positive control batch.

d) Production of the sera

One hundred and eighty minutes later, all the mice were punctured through the retroorbital sinuses on dry tubes. As soon as the blood coagulates, the clot is detached. The blood is centrifuged for 10 minutes at 1800 g at a temperature of 10° C.

The sera, once collected, are frozen at −25° C.

2 —DAYNES technique a) Dosage

Three dosages are studied

40 μg of PIV in 0.2 ml of physiological saline—that is to say 200 μg/ml

25 Ag of PIV in 0.2 ml of physiological saline—that is to say 125 μg/ml

10 μg of PIV in 0.2 ml of physiological saline—that is to say 50 μg/ml b) Treatment of the animals It was carried out on mice separated into 5 batches of 5 animals one negative control batch
one positive control batch
three PIV batches (1 per dosage)

The animals in the control batches receive an injection of 0.2 ml of physiological saline intravenously.

The animals in the PIV batches receive an injection of the product at various dosages intravenously. (Caudal vein)

c) Induction of IL1α

Immediately afterwards, a sublethal dose of LPS (1.2 mg years [sic] 0.2 ml of physiological saline) is injected intraperitoneally into each animal in the PIV batches and into the positive control batches.

d) Production of the sera

One hundred and eighty minutes later, all the mice are punctured through the retroorbital sinuses on dry tubes. As soon as the blood coagulates, the clot is detached. The blood is centrifuged for 10 minutes at 1800 g at a temperature of 10° C. The sera once collected are frozen at −25° C.

3—Assay of IL1α

The Interleukin-1α contained in these sera is assayed 24 hours after the sampling with the murine IL1α ELISA assay Kit (ref. 1900 GENZYME)

Rapid description of the Kit: the method used for this assay is of the sandwich type.

A first anti-murine IL1α monoclonal antibody is used

The samples are then deposited, then a second biotinylated anti-IL1α antibody is caused to react.

The revealing takes place with avidin coupled to peroxydase.

The coloured reaction uses tetramethylbenzidine (TMB)

The reading is made at 450 nm on a MULTISKAN MCC 340 MKII (TITERTEK) plate reader.

The results obtained by the SHEENAN method are presented in Table 1 below:

TABLE 1

| | Mean value For the positive control | Percentage of activity of PIC per dosage | | |
|---|---|---|---|---|
| | (in pg/ml) | 200 μg/ml | 125 μg/ml | 50 μg/ml |
| STUDY 1 | 250 | −94% | −50% | −82% |
| STUDY 2 | 230 | −50% | −46% | −31% |
| STUDY 3 | 200 | −62% | −37% | −47% |
| STUDY 4 | 430 | −62% | −49% | −76% |
| STUDY 5 | 430 | −38% | −62% | −58% |

The mean decreases in IL1α obtained per dosage are of the order of 55% (60% at 200 μg/ml, 50% at 125 μg/ml and 50% at 50 μg/ml) for all the five studies.

All the results obtained confirm the anti-inflammatory activity of PIV, through its IL1α synthesis inhibiting action.

Indeed, with the two methodologies used, a decrease in the synthesis of Interleukin-1α of at least 50% relative to the control is observed.

This anti-inflammatory activity was complemented by a study of the immunosuppressive activity of PIV against Tumor Necrosis Factor-α.

The results obtained (−40%) confirm the suppressive activity of PIV on the synthesis of Interleukin IL1 and INF-α.

Protection of the treated animals which had received a lethal dose of LPS was also observed: this protection resulting in a highly significant retarded mortality rate.

EXAMPLE 9
Inhibition of the activity of TNF-α by the Peptide PIV

Materials and method

The DAYNES techniques described in Example 8 are used.

DAYNES technique a) Dosage

Three dosages are studied

40 µg of PIV in 0.2 ml of physiological saline—that is to say 200 µg/ml

25 µg of PIV in 0.2 ml of physiological saline—that is to say 125 µg/ml

10 µg of PIV in 0.2 ml of physiological saline—that is to say 50 µg/ml b) Treatment of the animals It was carried out on mice separated into 5 batches of 5 animals one negative control batch
one positive control batch
three PIV batches (1 per dosage)

The animals in the control batches receive an injection of 0.2 ml of physiological saline intravenously. The animals in the PIV batches receive an injection of the product at various dosages intravenously. (Caudal vein)

c) Induction of TNF-α

Immediately after the treatment of the mice, a sublethal dose of LPS (1.2 mg in 0.2 ml of physiological saline) is intraperitoneally injected into each animal in the batches and positive control.

d) Production of the sera

Ninety minutes later, all the mice are punctured through the retroorbital sinuses on dry tubes. As soon as the blood coagulates, the clot is detached. The blood is centrifuged for 10 minutes at 10° C. at 1800 g.

The sera once collected are frozen at −25° C.

Assay of TNF-α

The TNF-α contained in these sera is assayed 24 hours after the sampling with the murine TNF-α ELISA assay Kit (ref. 1509-00 GENZYME)

Rapid description of the Kit: the method used for this assay is of the sandwich type.

A first anti-murine TNF-A monoclonal antibody is used.

The samples are then deposited and then a second anti-TNF-α goat antibody is caused to react.

The revealing takes place with a peroxidase-labelled anti-goat immunoglobulin donkey antibody.

The colored reaction uses o-phenylenediamine (OPD).

The reading is made at 492 nm with a plate reader (TITERTEK MKII MCC 340)

The results obtained are presented in Table 2 below:

TABLE 2

| | Mean Value For the positive control (in pg/ml) | Percentage of activity of PIV per dosage | | |
|---|---|---|---|---|
| | | 200 µg/ml | 125 µg/ml | 50 µg/ml |
| STUDY 1 | 2600 | −41% | −26% | −31% |
| STUDY 2 | 4690 | −65% | −53% | −38% |
| STUDY 3 | 4690 | −52% | −45% | −42% |
| STUDY 4 | 4040 | −30% | −41% | −41% |
| STUDY 5 | 4360 | −42% | −34% | −31% |

This methodology confirms the mean results obtained above.

Indeed, mean decreases in TNF-α which are obtained per dosage are of the order of 40% (46% at 200 µg/ml, 40% at 125 µg/ml and 37% at 50 µg/ml) for all the five studies.

EXAMPLE 10

Study of the Anti-allergic activity of the Peptide compounds, by the Dinitrofluorobenzene (DNFB) contact Hypersensitivity test.

Materials and methods

Compound 3 "PIII" Batches 1 - 2 - 3

Compound 4 "PIV" Batches 4 - 5 - 6

Female C57 BL/6JICO mice 5 weeks old are separated into ten batches of ten animals (five per cage), with free access to water and food, subjected to a photoperiod of twelve hours of light per twenty-four hours.

The animals in batches 1 to 6 receive daily and per topical application on the shaved skin of the back, the products to be studied, dissolved in propylene glycol, in a constant volume of 50 µl and for five consecutive days.

Dosage per mouse and per day

PIII—Batches 1 - 2 - 3—2.5 µg —0.5 µg—0.1 µg—mouse/day

PIV—Batches 4 - 5 - 6 - 2.5µg—0.5 µg—0.1 µg—mouse/day

The animals of the X batch serve as controls (and receive only, 50 µl of propylene glycol per topical application for five days).

On the fifth day, thirty minutes after the last application, all the mice are sensitized with 25 µl of DNFB (2.4-Dinitro-1-FluoroBenzene (FLUKA CHEMIKA PURUM at 97% batch No. 33820890) at 2% in a 4 to 1 mixture of acetone (SDS ref. 0510) and triolein (FLUKA) applied topically over the dorsal region of shaved skin.

On the sixth day, a new sensitization is carried out by application of DNFB.

On the eleventh day, the thickness of the ears of the mice is measured with the aid of a micrometer (ROCH 0 to 25 mm in $\frac{1}{100}$ mm) in order to obtain base values, then the ears are stimulated by topical application of 20 µl of DNFB at 0.8%.

On the twelfth day, the thickness of the ears is again measured. The mean value of thickening of the ears is established for the mice in the batches which had received the products to be studied, as well as for the mice in the control batch.

The percentage of suppression where appropriate will be expressed by the following calculation:

$$\frac{C-S}{C} \times 100$$

The results are presented in Tables 3 to 6 below:

TABLE 3

PIII Results

| PIII BATCHES | NUMBER OF MICE | SENSITIZATION | STIMULATION | RESULTS LEFT EAR % INCREASE | MEAN VALUES RIGHT EAR % INCREASE |
|---|---|---|---|---|---|
| BATCH 1 PIII (S1) 2.5 μg/mouse/day | 10 | BACK 2% DNFB | EARS 0.8% DNFB | 19.21 | 19.21 |
| BATCH 2 PIII (S1) 0.5 μg/mouse/day | 10 | BACK 2% DNFB | EARS 0.8% DNFB | 19.81 | 19.81 |
| BATCH 3 PIII (S1) 0.1 μg/mouse/day | 10 | BACK 2% DNFB | EARS 0.8% DNFB | 17.71 | 17.71 |
| BATCH X Controls | 10 | BACK 2% DNFB | EARS 0.8% DNFB | 58.92 | 58.92 |

TABLE 4

PIV Results

| PIV BATCHES | NUMBER OF MICE | SENSITIZATION | STIMULATION | RESULTS LEFT EAR % INCREASE | MEAN VALUES RIGHT EAR % INCREASE |
|---|---|---|---|---|---|
| BATCH 4 PIV (S2) 2.5 μg/mouse/day | 10 | BACK 2% DNFB | EARS 0.8% DNFB | 17.99 | 17.99 |
| BATCH 5 PIV (S2) 0.5 μg/mouse/day | 10 | BACK 2% DNFB | EARS 0.8% DNFB | 18.03 | 18.03 |
| BATCH 6 PIV (S2) 0.1 μg/mouse/day | 10 | BACK 2% DNFB | EARS 0.8% DNFB | 20.35 | 20.35 |
| BATCH X Controls | 10 | BACK 2% DNFB | EARS 0.8% DNFB | 58.92 | 58.92 |

TABLE 5

PIII Results
Percentage suppression of "DNFB" contact hypersensitivity
% suppression relative to the control batch
according to the formula:

$$\frac{C - S}{C} \times 100$$

| BATCH 1 (S1) 2.5 μg/mouse/day | | BATCH 2 (S1) 0.5 μg/mouse/day | | BATCH 3 (S1) 0.1 μg/mouse/day | |
|---|---|---|---|---|---|
| LEFT EAR | RIGHT EAR | LEFT EAR | RIGHT EAR | LEFT EAR | RIGHT EAR |
| −67.40 | −67.40 | −66.38 | −66.38 | −69.94 | −69.94 |

TABLE 6

PIV Results
Percentage suppression of "DNFB" contact hypersensitivity
% suppression relative to the control batch
according to the formula:

$$\frac{C - S}{C} \times 100$$

| BATCH 4 (S2) 2.5 μg/mouse/day | | BATCH 5 (S2) 0.5 μg/mouse/day | | BATCH 6 (S2) 0.1 μg/mouse/day | |
|---|---|---|---|---|---|
| LEFT EAR | RIGHT EAR | LEFT EAR | RIGHT EAR | LEFT EAR | RIGHT EAR |
| −69.47 | −69.47 | −69.40 | −69.40 | −65.46 | −65.46 |

PIII and PIV suppress in a highly significant manner—"67.90% and 68.11%" the cutaneous hypersensitivity reaction induced by the administration of DiNitroFluoroBenzene under the experimental conditions described above.

EXAMPLE 11

Study of the anti-inflammatory activity of PIII and PIV

1) Aim of the study:

The demonstration of the inhibitory effect of the peptides PIII and PIV on the production, by fibroblasts stimulated by IL1, of a metabolite of arachidonic acid, PGE2.

2) Methods:

2-1 Culture of embryonic pulmonary fibroplasts [sic] of human origin:

We chose to use the strain ATCC MRC5 maintained in the laboratory continuously and already tested by Cannon et al. (J. Immunol., 1986).

After subculturing, the fibroplasts [sic] are cultured in microwells (24-well plate of 2 cm2, Falcon). The innoculum is 30 000 cells per well; the nutrient medium used is composed of RPMI 1640 (90%) and of complement-free fetal calf serum (FCS, 10%). The medium is changed every two days until the cells become confluent.

2—2 Setting up of the experiment

The monocell layers thus obtained are washed and pre-incubated for 24 hours in fresh medium containing only 1% of FCS. The substances to be tested are added to the medium at various concentrations of between $10^{-6}$ and $10^{-4}M$. After incubating for 20 minutes in the presence of these compounds, human recombinant IL1 (Tebu, France) at a concentration of 5, 2.5 or 0.5 ng/ml of medium is placed in contact with cells for 18 hours.

At the end of this incubation, the supernatants are collected and frozen at $-80°$ C. until the analysis is carried out. The monocell layers are fixed with methanol.

2—3 Assay of PGE2

The RIA assay is carried out according to the method described by Dray et al. (Europ. J. Invest. 1975). 3 series of experiments, in duplicate, were carried out for each concentration of product studied and for the controls. The results are expressed in pg/μg of DNA. The inhibitory effect is expressed in percentage relative to the controls.

In order to avoid any possible error due to the counting by optical microscopy, the DNA was assayed by a fluorimetric method according to the procedure described by Brunk et al. (Analytical Biochem., 1979).

Table 7 below presents the 1st series of trials on the strain MRC5

TABLE 7

| | Action of PIII | |
|---|---|---|
| PIII Samples | PGE2 pg/μg of DNA | % inhibition |
| IL1:2.5 ng | 389 ± 60 | |
| +PIII $10^{-4}$ M | 179 ± 50 | 53 |
| +PIII $10^{-5}$ M | 232 ± 45 | 40 |
| +PIII $10^{-6}$ M | 292 ± 68 | 24 |
| +PIII $10^{-7}$ M | 364 ± 68 | 6 |
| +PIII $10^{-8}$ M | 335 ± 50 | 13 |
| +PIII $10^{-9}$ M | 320 ± 43 | 17 |
| IL1:0.5 ng | 288 ± 25 | |
| +PIII $10^{-4}$ M | 113 ± 25 | 60 |
| +PIII $10^{-5}$ M | 176 ± 37 | 38 |
| +PIII $10^{-6}$ M | 231 ± 55 | 19 |
| +PIII $10^{-7}$ M | 249 ± 60 | 13 |
| +PIII $10^{-8}$ M | 258 ± 35 | 10 |
| +PIII $10^{-9}$ M | 364 ± 56 | no inhibition |

A good inhibitory action of PIII was observed with a dose-effect relationship. This action does not depend on the IL1 concentration. No action was observed starting from $10^{-7}M$ in both cases.

TABLE 8

| | Action of PIV | |
|---|---|---|
| PIV Samples | PGE2 pg/mg of DNA | % inhibition |
| IL1:5 ng | 7576 ± 310 | |
| +PIV $10^{-4}$ M | 2964 ± 184 | 60 |
| +PIV $10^{-5}$ M | 4580 ± 230 | 38 |
| +PIV $10^{-6}$ M | 4900 ± 340 | 34 |

TABLE 8-continued

| | Action of PIV | |
|---|---|---|
| PIV Samples | PGE2 pg/mg of DNA | % inhibition |
| +PIV $10^{-7}$ M | 6150 ± 365 | 17 |
| +PIV $10^{-8}$ M | 6142 ± 255 | 17 |
| +PIV $10^{-9}$ M | 5047 ± 279 | 32 |

PIII and PIV possess an inhibitory power on the action of IL1 and of PGE2.

This very significant action may be linked to a blocking of the receptors.

EXAMPLE 12

Study of the action of PIII and PVI on mouse melanorenesis after topical application in the form of a dermal cream (Warren Technique).

Materials and method

1) Materials

Compound 3 PIII

[(DL) Lip] - Glu - His - ParaFPhe - Arg - Trp - Gly - NH2

Compound 6 PIV

[N.Lipoyl - Lysine] - His - D.homoPhe - Arg - Trp - Gly - NH2

Dermal excipient No. 66

Lano—petroleum jelly—Ac

Liquid paraffin

Beeswax Ethoxyl [sic]

Purified lanolin

PEG—200

Dermal formulas

Peptides PIII and PVI incorporated in an amount of 5% into the dermal excipient No. 66

Animals

DBA/2 mice IFFA—CREDO 5 weeks old

2) Methods

A dorsal tonsure is delimited on each animal after epilation

The products to be tested are applied by massaging at a rate of 2 applications per day of 50 μl of each preparation for 5 days Two days after the last application, the animals are sacrificed and about 50 mg fractions of treated skin are collected.

Each sample is dried by freeze-drying and weighed

The skin fragments are then subjected to an enzymatic hydrolysis by protease K for 72 hours at 45° C. (Protease K Merck—24.568)

500 μl of Na2CO3 and 20 μl of H202 at 35% are added to the hydrolysates obtained The incubation is carried out for 30 minutes at 80° C.

After cooling, 200 μl of chloroform/methanol (2 vol/1 vol) are added to each sample The mixture is centrifuged at 10 000 g The aqueous phase (200 μl) is distributed into the wells of a "NUNC" microplate Assay of Melanin The assay of melanin is carried out at 405 nm with the aid of a Multiskan—Titertek—MCC—340, in comparison with a calibration series consisting of Sigma M.8631 melanin Results They are expressed in percentage of melanin in comparison with the excipients considered as controls I—Cream PIII—5 $10^{-5}M$ of PIII for 50 μl of cream II—Cream PVI—5 $10^{-5}M$ of PVI for 50 μl of cream III—Excipient 66 - as control C
Mean of the results on 15 assays

TABLE 9

| Samples | % of Melanin in mg |
|---|---|
| I Cream PIII | 4 mg % of melanin |
| II Cream PVI | 71 m % of melanin |
| III Excipient 66 - Control | 0 mg % of melanin |

Percentage of stimulation
QS=mean quantity of melanin per mg of skin—Sample
QC=mean quantity of melanin per mg of skin—Control $$\% \text{ stimulation} = \frac{QS - QC}{QC} \times 100$$

The dermal cream containing PVI administered topically induces in a highly significant manner the synthesis of Melanin in the epidermis (+71%).

This activity, which is in accordance with the subject of the present invention, is linked to the chemical structure of PVI which contains N.Lipoyl—Lysine and D.homoPhenyl groups.

The dermal cream whose formula contains PIII administered topically has no activity on the stimulation of Epidermal Melanogenesis, this absence of activity is linked to the presence, in the structure of PIII, of the "para.FluoroPhenyl" group in accordance with the subject of the present invention.

These results were confirmed by a study on Melanogenesis according to the "CLOUDMAN" technique by in vitro culture of melanocytes using CLOUDMAN's melanoma cells in rats.

All the results obtained are in accordance with the subject of the present invention of which the objective is the production of peptide derivatives which are active via the Topical route and whose anti-allergic and anti-inflammatory activities can be separated from the activity on Melanogenesis according to the applications envisaged.

EXAMPLE 13
Comparative study of the activity of Lipoyl-Peptides and of their peptide structures on DNFB contact hypersensitivity.
Materials and method
The method used is that described above in Example 10.
Contact hypersensitivity induced in mice by Dinitrofluorobenzene—"DNBF"
Products studied
Batch I: (DL) - Lip - Glu - His - D.homoPhe - Arg - Trp - Gly - NH2
Batch II: H - Glu - His - D.homoPhe - Arg - Trp - Gly - NH2
Batch III: Control=(DL) - Lipoic Acid
Solvent: propylene Glycol previously used as control in Example 10.
Measurement of the activity of the control will be carried out for each experiment.
Experiment and dosage
Batch I: doses used
1=1 µg/mouse/day
2=10 µg/mouse/day
3=100 µg/mouse/day
Batch II: doses used
4=1 ng/mouse/day
5=10 ng/mouse/day
6=100 ng/mouse/day Control: dose used"DL-Lipoic-Acid"=10 ng per mouse and per day.

On the fifth day, thirty minutes after the last application, all the mice were sensitized with 25 µl of DNFB (2.4-Dinitro-1-FluoroBenzene (FLUKA CHEMIKA PURUM at 97% batch No. 33820890) at 2% in a 4 to 1 mixture of acetone (SDS ref. 05510) and triolein (FLUKA) applied topically over the dorsal region of shaved skin.

On the sixth day, a new sensitization is carried out by application of DNFB.

On the eleventh day, the thickness of the ears of the mice is measured with the aid of a micrometer (ROCH 0 to 25 mm in 1/100 mm) in order to obtain base values, then the ears are stimulated by topical application of 20 µl of DNFB at 0.8%.

On the twelfth day, the thickness of the ears is again measured. The mean value of thickening of the ears is established for the mice in the batches which had received the products to be studied, as well as for the mice in the control batch. The percentage of suppression where appropriate will be expressed by the following calculation:

$$\frac{C - S}{C} \times 100$$

TABLE 10

MICE: CONTACT HYPERSENSITIVITY
SUMMARY TABLE BATCH I

| BATCHES | NUMBER OF MICE | SENSITIZATION | STIMULATION | RESULTS LEFT EAR MEAN % INCREASE | MEAN RIGHT EAR MEAN % INCREASE |
|---|---|---|---|---|---|
| Batch I: 100 ng/mouse/day | 10 | Back 2% DNFB | Ears 0.8% DNFB | 11.66 | 11.66 |
| Batch I: 10 ng/mouse/day | 10 | Back 2% DNFB | Ears 0.8% DNFB | 12.95 | 13.01 |
| Batch I: 1 ng/mouse/day | 10 | Back 2% DNFB | Ears 0.8% DNFB | 13.86 | 13.86 |
| Controls | 10 | Back 2% DNFB | Ears 0.8% DNFB | 56.34 | 56.75 |

TABLE 11

MICE BATCH I
CONTACT HYPERSENSITIVITY - DNFB
% SUPPRESSION RELATIVE TO THE CONTROL BATCH
ACCORDING TO THE FORMULA:
$\frac{C - S}{C} \times 100$

| Batch I: 100 ng/mouse/day | | Batch I: 10 ng/mouse/day | | Batch I: 1 ng/mouse/day | |
|---|---|---|---|---|---|
| Left Ear | Right Ear | Left Ear | Right Ear | Left Ear | Right Ear |
| −79.30 | −79.45 | −77.01 | −76.90 | −75.40 | −75.58 |

TABLE 12

MICE: CONTACT HYPERSENSITIVITY - DNFB
SUMMARY TABLE BATCH II

| BATCHES | NUMBER OF MICE | SENSITIZATION | STIMULATION | RESULTS LEFT EAR MEAN % INCREASE | MEAN RIGHT EAR MEAN % INCREASE |
|---|---|---|---|---|---|
| Batch II: 1 ng/mouse/day | 10 | Back 2% DNFB | Ears 0.8% DNFB | 37.07 | 37.07 |
| Batch II: 10 ng/mouse/day | 10 | Back 2% DNFB | Ears 0.6% DNFB | 34.84 | 34.84 |
| Batch II: 100 ng/mouse/day | 10 | Back 2% DNFB | Ears 0.8% DNFB | 43.10 | 43.10 |
| CONTROL BATCH | 10 | Back 2% DNFB | Ears 0.8% DNFB | 58.92 | 58.92 |

TABLE I3

MICE: CONTACT HYPERSENSITIVITY - DNFB
% SUPPRESSION RELATIVE TO THE CONTROL BATCH
ACCORDING TO THE FORMULA:

$$\frac{C - S}{C} \times 100$$

| Batch II: 1 ng/mouse/day | | Batch II: 10 ng/mouse/day | | Batch II: 100 ng/mouse/day | |
|---|---|---|---|---|---|
| Left Ear | Right Ear | Left Ear | Right Ear | Left Ear | Right Ear |
| 37.08 | 37.08 | 40.83 | 40.87 | 27.15 | 27.15 |

Results
Batch I—Lipoyl-Peptide—I
79% suppression of cutaneous hypersensitivity is observed at the dose of 100 ng/mouse/day.
A clear dose/effect relationship is also observed between the doses of 1 ng - 10 ng and 100 ng.
Batch II—Peptide alone
40% suppression of cutaneous hypersensitivity is observed at the dose of 10 ng/mouse/day.
For the doses of 1 ng and of 100 ng, the suppressive response is of the order of 37.08 and 27.15%, without being able to observe a dose/effect type relationship.
Control batch—Lipoic Acid alone
No suppressive effect of cutaneous hypersensitivity is observed on administration of Lipoic acid, in solution in Propylene - Glycol.
Administered topically and under the experimental conditions described, the "Lipoyl Peptide" structure induces in a highly significant manner the suppression of cutaneous hypersensitivity in mice.

EXAMPLE 14

Embryo-Toxicology
Qualitative and quantitative analysis of the effects of PIV on melanocyte differentiation in in vitro culture. Sample to be analyzed—compound 4=PIV
Biological materials
Embryonic cells isolated in in vitro culture in a defined, purely saline medium (standard culture conditions: 2 ml of medium/culture).

The embryonic territory is collected (from Triton embryo and from Axolotl embryo) from the first stage of melanogenesis, immediately after melanocyte induction.
At this early stage of embryonic development, the neural swelling, which has just become individualized, contains all the melanoblastic precursors. The culture of the cells of the neural swelling and of the underlying mesoderm makes it possible to coculture (under completely identical conditions) the melanoblasts with various other cell precursors belonging to various categories: neuroblasts, myoblasts, epidermal cells, fibroplasts [sic], mesenchymatous cells.
This allows a comparative kinetic study, on a living material, of the effects of PIV on the melanocytes and various other cell types.
Duration of the culture (primary culture): 2 to 3 weeks at 20° C.
The cell differentiation appears morphologically from the 3rd day and is practically complete at 8–10 days of culture.
Treatments
1 Dose/response trials
A series of PIV concentrations was analyzed:
0.01 $\mu$g/ml; 0.1 $\mu$g/ml; 1 $\mu$g/ml; and 10 $\mu$g/ml
0.01 $\mu$g/ml: no effect
1 $\mu$g/ml: optimal effect on melanocyte differentiation (according to the criteria indicated in "Results")
The following 2 doses were therefore selected for this work: 0.1 and 1 $\mu$g/ml.
2 Treatments
1 single treatment during the innoculation of cultured cells. After their attachment (3 days at 20° C.), the medium is replaced with fresh medium without the Peptide PIV
1 treatment during the innoculation and a 2nd treatment during the change of medium.
Results
Effects of a qualitative nature
1) Stimulating effect of PIV on melanogenesis
2) This effect is not accompanied by cytotoxicity phenomena.
3) The other categories of cultured cells are not affected; their morphology and their differentiation progress normally, except those of the neurons which have neurite extensions which are shorter and in a denser network than in the control. It should be noted that these neurons are derived from the neural crest (neural swelling) and are therefore the neurones at the origin of the peripheral nervous system.
4) No toxic effect is observed; all the cells, other than the melanoblasts, differentiate and develop like the untreated control cells.
Quantitative analyses
The following effect of PIV on melanogenesis is manifested not only by an increase in the size of the melanocytes (cf. plate I and II) but also:
5) by an increase in their number;
6) by an increase in the quantity of biosynthesized melanin.
A—Stimulating effect of PIV on melanogenesis
1) It is already important to emphasize that the stimulating effects described above manifest themselves in a similar manner after 2 treatments or a single treatment (in this case, the cells are maintained in the presence of PIV for only the first 2 days of culture when they are still morphologically undifferentiated melanoblasts. It is not therefore necessary, in order to have an optimum stimulation, to maintain these cells in the presence of PIV for the entire period of their differentiation.

The stimulating effect of PIV manifested itself in a completely identical manner on the embryonic cells of Tritons as well as of Axolotl.

2) Phenotypic differentiation of the melanocytes appears more rapidly in the treated cultures (from the 2nd day after innoculation) than in the control cultures.

3) The stimulation of melanogenesis affects the size of the melanocytes which increases by a factor×4 and even×5 after 8 days of culture for a treatment with 1 µg/ml.

4) The stimulating effect of PIV also affects the quantity of biosynthesized melanin.

Already the sole observation, on a living material, of the treated melanocytes makes it possible to observe that they are much darker, in spite of their larger size, than the control melanocytes.

We developed two melanin assays:
by HPLC with electrochemical detection
by spectrophotometry (by adaptation of the method of TOMITA et al. 1990) at 470 nm.

The development of these assays was carried out using standard solutions of melanin (Sigma, ref. M 8631) in order to define the comparative sensitivity and the minimum level of detection by either of the methods. The µg is the minimum level which can be assayed by spectrophotometry; the ng is the lower level which can be assayed by HPLC.

It should however, be observed that these two techniques, especially the spectrophotometric assay, can be used since, for our cell cultures, 15 embryonic explants associated in culture are sufficient to allow quantification (by spectrophotometry).

TABLE 14

|  | Control cultures (15 explants) | Treated cultures (15 explants) | Stimulation |
|---|---|---|---|
| 1st experiment | 830 ng/explant | 2120 ng/explant | ×2.5 |
| 2nd experiment | 950 ng/explant | 2150 ng/explant | ×2.3 |
| 3rd experiment | 1820 ng/explant | 2710 ng/explant | ×1.5 |
| 4th experiment | 1913 ng/explant | 4782 ng/explant | ×2.5 |

It should be noted that the treated melanocytes show no apparent sign of cytotoxicity. Furthermore, they have a life which is equivalent to that of the control melanocytes in vitro.

B—Effects of piv on the other cocultured cell categories

Ciliated and non-ciliated epidermis cells, mesenchymatous cells, fibroblasts:
no specific cell proliferation
no stimulating effect on their size, their spreading and the like
no cytotoxic effect
no retardation or accelaration in their differentiation, nor their behaviour in vitro.

Neuroblasts (embryonic origin of the PNS):
no specific stimulating effect on the number of neurons or on the size of the cell bodies (plate II, A).

Effect on the morphology of the neurite network:
As a whole, the neurite network in the treated cultures consists of neurites which are shorter and more dispersed than the control neurites.

This observation should be analyzed more finely.

All the observations and quantifications were carried out on several experimental series in order to perfectly control the reproducibility of the phenomena described.

EXAMPLE 15

Effects of Peptides PI and PIV on cultured embryonic cells in vitro . . . "Melanocytes - Neurons - Muscular Cells and Fibroblasts . . . "

Materials and methods
The experimental conditions developed are the following:
dose used 1 µg/ml (defined by dose/response trials)
1 single treatment during the innoculation of the cells or several successive treatments (renewal of the medium every 48 hours)
duration of culture: 6 to 8 days
quantification
1) Counting of the melanocytes
2) Assay of melanin by HPLC and/or by spectrophotometry
Daily observation of the cultures
Ultrastructure by transmission electron microscopy.
Stimulating effects of PI and of PIV on melanogenesis The treatment, with PI and PIV, of the embryonic cells which are precursors of the melanocytes, stimulates their differentiation both from a qualitative point of view and from a quantitative point of view. The number of melanocytes increases at least by a factor 2 by culturing.

The quantity of biosynthesized melanin per cell also increases by an equivalent factor (1.4 ng/cell) after eight days of culture.

Preliminary trials of study by confocal microscopy with the TITN - ALCATEL SAMBA 2005 system show that it will be possible to analyze the melanin particles (melanosomes) themselves.

The peptide PI and PIV formulas stimulate the differentiation of the melanoblasts. It is important to emphasize the following remarkable result. They do not stimulate the precurser embryonic cells which have not yet been determined in the melanoblastic pathway. They are not therefore inducers and have only the melanoblast as target: no effect on the precursor cells; stimulating effect on the melanoblasts already induced).

Analysis of the cytotoxicity of PI and PIV
Neuroblasts
The two peptide formulas studied have no toxic or stimulating effect on the neuroblasts or the neurons.

The size of the cell bodies, the length and the number of neurites, the ultrastructure and finally the life of the treated neurons are equivalent to those of the control neurons.

Glial cells (astrocytes)
No toxic effect is observed on the astroglial cells treated with PI and PIV which differentiate normally and without retardation compared to the control astrocytes.

Myoblasts
Here also, no toxic effect is detected even at an ultrastructural level.

The myoblasts spread and differentiate without retardation and without abnormality compared to the control myoblasts.

Fibroblasts, mesenchyme
Similar results are obtained: no toxic effect is observed.

All the cytology and biochemistry work on the PI and PIV effects on melanogenesis on the one hand and on the differentiation of various other cell categories on the other hand demonstrates that:

PI and PIV stimulate melanogenesis both from the qualitative point of view and from the quantitative point of view.

PI and PIV are without stimulating effect on the other cell types studied: neurons, astrocytes, muscle cells, fibroplasts [sic], and the like.

PI and PIV have no cytotoxic effect on these various cell categories which differentiate and develop quite normally.

We claim:

1. A compound comprising a peptide of at least 4 amino acids including the following sequence: His Phe* Arg, wherein Phe* represents phenylalanine, homophenylalanine, halogenated phenylalanine or halogenated homophenylalanine and the amino acids are in the D, L or DL form, the N-terminal of said peptide being conjugated with thioctic acid, dihydrolioic acid, or N-lipoyl-lysine, in the form of the corresponding salts, esters or amides.

2. The compound according to claim 1, characterized in that one or more of the amino acids are glycosylated or sulfated.

3. The compound according to claim 1, characterized in that it has the formula:

X-His-Phe*-Arg-Y in which

Lip is a thioctyl, dihydrolipoyl or N-lipoly-lysyl,

X is Glu or a direct bond between Lip and His,

Y is selected from the group consisting of:

Trp - Gly - OH,

Trp - Gly - NH2,

Trp - NH2, and

Trp - OH and

Phe* is homoPhe or p-fluoroPhe, the amino acids being in D, L or DL form.

4. The compound according to claim 1, characterized in that it contains at least one of the following sequences:

| | |
|---|---|
| Glu-His-(D)homoPhe-Arg-Trp-Gly-NH2 | I |
| Glu-His-(D)homoPhe-Arg-Trp-Gly-NH2 | II |
| Glu-His-para-fluoroPhe-Arg-Trp-Gly-NH2 | III |
| His-(D)homoPhe-Arg-Trp-NH2 | IV |
| Glu-His(D)homoPhe-Arg-Trp-Gly-NH2 | V |
| His-(D)homoPhe-Arg-Trp Gly-NH2; or | VI |
| His(D)homoPhe-Arg-Tr NH2 | VII | as well as the derivatives of these molecules in the form of salts of esters or of amides.

5. The compound according to claim 3, characterized in that one or more of the amino acids are glycosylated or sulfated.

6. The compound according to claim 4, characterized in that one or more of the amino acids are glycosylated or sulfated.

7. A pharmaceutical composition containing as active ingredient at least one compound according to claim 4.

8. The pharmaceutical composition according to claim 7, characterized in that it is formulated as to be administered orally or intraperitoneally.

9. The pharmaceutical composition according to claim 7, characterized in that it is formulated as to be administered via an external topical route.

10. A dermo-cosmetic composition containing at least one compound according to claim 4.

11. A pharmaceutical composition containing as active ingredient at least one compound according to claim 1.

12. The pharmaceutical composition according to claim 11, characterized in that it is formulated as to be administered orally or intraperitoneally.

13. The pharmaceutical composition according to claim 11, characterized in that it is formulated as to be administered via an external topical route.

14. A dermo-cosmetic composition containing at least one compound according to claim 1.

15. The compound of claim 1, wherein Phe* is homophenylalanine, halogenated phenylalanine or halogenated homophenylalanine.

16. The compound of claim 1, wherein the peptide includes the sequence GluIisPhe*Arg, and wherein said Glu residue includes said conjugated N-terminal.

17. An anti-allergic or anti-inflammatory compound comprising a peptide of four to six amino acids including the following sequence:

His Phe* Arg, wherein the amino terminus is acylated with thioctic acid dihydrolipoic acid, or N-lipoyl-lysine, Phe* represents phenylalanine, homophenylalanine, halogenated phenylalanine or halogenated homophenylalanine, and the amino acids are in the D, L, or DL form, and pharmaceutically acceptable salts esters or amides of said peptide.

18. The compound of claim 17, wherein Phe* is homophenylalanine, halogenated phenylalanine or halogenated homophenylalanine.

19. A method of treating an allergy or inflammatory reaction in an animal comprising: administering to the animal an allergy treating or inflammatory reaction treating effective amount of:

a compound containing a peptide of at least 4 amino acids including the following sequence: His Phe* Arg, wherein Phe* represents phenylalanine, homophenylalanine, halogenated phenylalanine or halogenated homophenylalanine, the N-terminus of said peptide being conjugated with thioctic acid, dihydrolioic acid, or N-lipoyl-lysine, in the form of the corresponding salts, esters or amides.

20. The method of claim 19, wherein an allergy treating or inflammatory reaction treating effective amount of a said compound which is sulfated or glycosylated.

21. The method of claim 19, wherein an allergy treating or inflammatory reaction treating effective amount of a said compound wherein Phe* is homophenylalanine, halogenated phenylalanine or halogenated homophenylalanine.

22. The method of claim 19, wherein an allergy treating or inflammatory reaction treating effective amount of a said compound wherein the peptide includes the sequence GluFisPhe*Arg, and wherein said Glu residue includes said conjugated N-terminal.

* * * * *